(12) United States Patent
Petersen

(10) Patent No.: US 8,231,649 B2
(45) Date of Patent: Jul. 31, 2012

(54) RETRIEVABLE BLOOD CLOT FILTER WITH RETRACTABLE ANCHORING MEMBERS

(75) Inventor: Scott Petersen, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1492 days.

(21) Appl. No.: 10/762,643

(22) Filed: Jan. 20, 2004

(65) Prior Publication Data

US 2005/0159771 A1    Jul. 21, 2005

(51) Int. Cl.
*A61F 2/01* (2006.01)
(52) U.S. Cl. ...................................... 606/200
(58) Field of Classification Search .......... 606/200, 606/194
See application file for complete search history.

(56) References Cited

U.S. PATENT DOCUMENTS

| | | | |
|---|---|---|---|
| 4,643,184 A | 2/1987 | Mobin-Uddin | |
| 4,781,177 A | 11/1988 | Lebigot | |
| 4,832,055 A * | 5/1989 | Palestrant | 128/899 |
| 4,969,891 A | 11/1990 | Gewertz | |
| 5,059,205 A * | 10/1991 | El-Nounou et al. | 606/200 |
| 5,071,407 A | 12/1991 | Termin et al. | |
| 5,133,733 A | 7/1992 | Rasmussen et al. | |
| 5,147,379 A * | 9/1992 | Sabbaghian et al. | 606/206 |
| 5,234,458 A | 8/1993 | Metais | |
| 5,242,462 A | 9/1993 | El-Nounou et al. | |
| 5,324,304 A | 6/1994 | Rasmussen | |
| 5,601,595 A | 2/1997 | Smith | |
| 5,626,605 A | 5/1997 | Irie et al. | |
| 5,669,933 A | 9/1997 | Simon et al. | |
| 5,746,767 A | 5/1998 | Smith | |
| 5,827,324 A | 10/1998 | Cassell et al. | |
| 5,836,968 A * | 11/1998 | Simon et al. | 606/200 |
| 5,836,969 A | 11/1998 | Kim et al. | |
| 5,853,420 A | 12/1998 | Chevillon et al. | |
| 5,984,947 A | 11/1999 | Smith | |
| 6,001,118 A | 12/1999 | Daniel et al. | |
| 6,007,558 A * | 12/1999 | Ravenscroft et al. | 606/200 |
| 6,066,158 A | 5/2000 | Engelson et al. | |
| 6,146,404 A | 11/2000 | Kim et al. | |
| 6,179,859 B1 | 1/2001 | Bates et al. | |
| 6,214,026 B1 | 4/2001 | Lepak et al. | |
| 6,217,600 B1 | 4/2001 | DiMatteo | |
| 6,231,589 B1 | 5/2001 | Wessman et al. | |
| 6,273,901 B1 * | 8/2001 | Whitcher et al. | 606/200 |
| 6,342,062 B1 * | 1/2002 | Suon et al. | 606/200 |

(Continued)

FOREIGN PATENT DOCUMENTS

WO    WO 2004/024032 A    3/2004

*Primary Examiner* — Ryan Severson
(74) *Attorney, Agent, or Firm* — Seager, Tufte & Wickhem LLC

(57) ABSTRACT

Retrievable blood clot filter devices implantable within a blood vessel, including methods and apparatuses for retrieving such devices, are disclosed. The retrievable blood clot filter device can include an apical head, and a plurality of elongated filter legs configured to expand between a collapsed position and an expanded position within the blood vessel. A bendable anchoring member disposed on one or more filter support members can be used to secure the blood clot filter device along the inner wall of the blood vessel. The anchoring members can be configured to bend and retract into a number of filter tubes slidably disposed along the support members, allowing the blood clot filter device to be removed with a retrieval apparatus.

22 Claims, 17 Drawing Sheets

U.S. PATENT DOCUMENTS

| | | |
|---|---|---|
| 6,375,670 B1 | 4/2002 | Greenhalgh |
| 6,391,044 B1 | 5/2002 | Yadav et al. |
| 6,443,972 B1 | 9/2002 | Bosma et al. |
| 6,447,530 B1 * | 9/2002 | Ostrovsky et al. ............ 606/200 |
| 6,482,221 B1 * | 11/2002 | Hebert et al. ................ 606/194 |
| 6,540,722 B1 | 4/2003 | Boyle et al. |
| 6,540,767 B1 | 4/2003 | Walak et al. |
| 6,540,768 B1 | 4/2003 | Diaz et al. |
| 6,558,405 B1 | 5/2003 | McInnes |
| 6,569,183 B1 | 5/2003 | Kim et al. |
| 6,569,184 B2 | 5/2003 | Huter |
| 6,616,680 B1 | 9/2003 | Thielen |
| 6,645,224 B2 | 11/2003 | Gilson et al. |
| 2002/0116024 A1 | 8/2002 | Goldberg et al. |
| 2003/0097145 A1 | 5/2003 | Goldberg et al. |
| 2004/0158274 A1 | 8/2004 | WasDyke |

* cited by examiner

RETRIEVABLE BLOOD CLOT FILTER WITH RETRACTABLE ANCHORING MEMBERS

FIELD OF THE INVENTION

The present invention relates generally to devices for filtering blood clots within a blood vessel. More specifically, the present invention pertains to retrievable blood clot filter devices and associated methods and apparatus for retrieving such devices within the body.

BACKGROUND OF THE INVENTION

Blood clot filters are used in combination with other thrombolytic agents to treat pulmonary embolism occurring within a patient. Such devices are generally inserted intravenously into a target location of the body (e.g. an artery or vein), and function by capturing blood clots (emboli) contained in the blood stream before they can reach the heart and/or lungs and cause permanent damage to the body. In the treatment of Deep Vein Thrombosis (DVT), for example, such filters are placed in the inferior vena cava to prevent further blood clotting in the large veins of the lower body. Placement of the filter is typically accomplished percutaneously via the femoral arteries or the jugular vein using a local anesthetic, or by performing a laparotomy with the patient under general anesthesia.

In certain designs, an introducer sheath may be used to deliver the blood clot filter through the body. Such introducer sheaths are generally tubular in shape, and include an inner lumen configured to transport the blood clot filter in a collapsed position through the body. Once transported to a desired location within the vasculature, the filter can then be removed from within the introducer sheath, allowing the filter to spring open and engage the vessel wall. A needle, hook, barb, prong, wedge or other attachment means disposed on the blood clot filter can be used to secure the filter to the vessel wall.

There are a number of situations in which it may be desirable for a physician to remove the filter once inserted within the body. In certain circumstances, for example, the risk of pulmonary embolism may be relatively short term (e.g. about two weeks), thus requiring insertion of the filter for only a short period of time. Permanent implantation of the filter in such cases may unnecessarily impede the flow of blood within the vessel, and can lead to further thrombosis growth at the filter implantation site. In other circumstances, it may be desirable to reposition the filter within the vessel, or to replace the existing filter with a new filter.

SUMMARY OF THE INVENTION

The present invention relates generally to retrievable blood clot filter devices implantable within a blood vessel. Associated retrieval apparatuses and methods for retrieving and/or repositioning the blood clot filter device within the body are also disclosed herein.

A retrievable blood clot filter device in accordance with an illustrative embodiment of the present invention may include an apical head, and a plurality of elongated filter legs configured to expand between a collapsed position and an expanded position within a blood vessel. One or more of the filter legs may include a bendable anchoring member that can be used to temporarily or permanently secure the blood clot filter device along the inner wall of the blood vessel. The anchoring members can be attached to or formed integrally with several support members that apply an outwardly directed force to the anchoring members. The anchoring members can be configured to retract within a number of filter tubes slidably disposed about the support members. In certain embodiments, a hub can be used to actuate the filter tubes about the anchoring members, causing them to disengage from the vessel wall and retract therein. Once retracted, the blood clot filter device can then be removed from the body, or repositioned at another location within the blood vessel and redeployed.

An illustrative retrieval apparatus configured to retrieve and/or reposition the blood clot filter device within the blood vessel is also disclosed herein. The retrieval apparatus can include an inner member configured to grasp the apical head, a middle tubular member configured to engage the hub and retract the anchoring members into the inner lumen of the filter tubes, and an outer sheath that can be used in collapsing and retrieving the blood clot filter device within the body. Various methods of retrieving the blood clot filter device using either a femoral or jugular approach are also described in detail herein.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
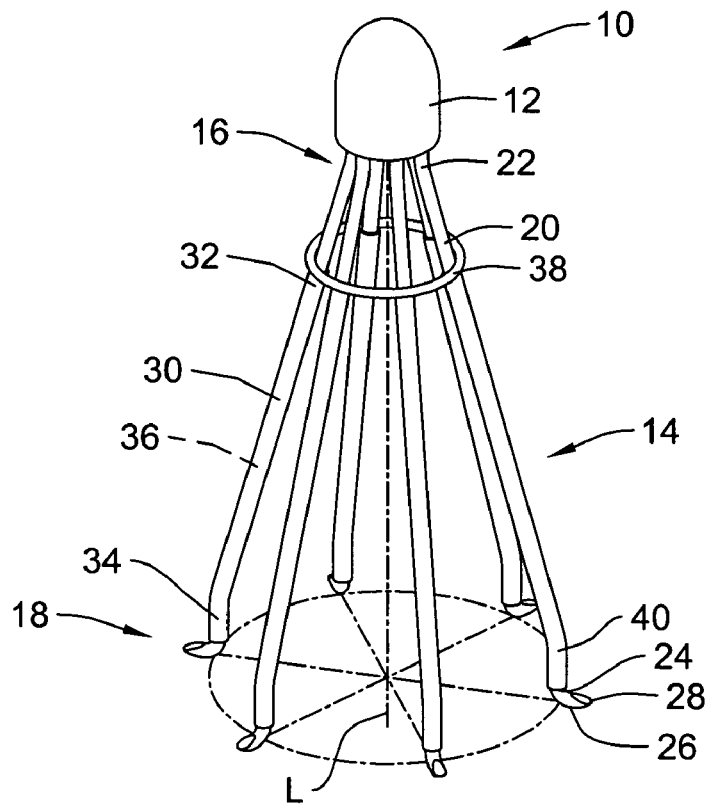
FIG. 1 is a perspective view showing a retrievable blood clot filter device in accordance with an illustrative embodiment of the present invention.

FIG. 1 is a perspective view of a retrievable blood clot filter device 10 in accordance with an illustrative embodiment of the present invention. Blood clot filter device 10 includes an apical head 12, and a plurality of elongated filter legs 14 each having a joined end section 16 and a free end section 18. Each of the filter legs 14 may be configured identically with respect to each other, and may be symmetrically spaced about a central longitudinal axis L in a generally conical-shaped configuration when expanded. The filter legs 14 may be collectively arranged about the longitudinal axis L such that the joined end section 16 of each filter leg 14 converges at the apical head 12 to form an apex. The filter legs 14 may be biased to expand from a substantially straight position when radially constrained within a delivery device to an outswept position when deployed in a blood vessel.

Each filter leg 14 may include a support member 20 having a first end 22 that is coupled to the apical head 12, and a distal end 24 that extends angularly in an outswept manner to a retractable anchoring member 26 disposed on the free end section 18 of each filter leg 14. The support member 20 may comprise a length of wire, rod, tubing, or other suitable member that can be formed into the shape depicted generally in FIG. 1.

To impart the desired amount of stiffness to the support members 20, a suitable metal or metal alloy such as platinum, gold, tantalum, tungsten, titanium, or stainless steel may be used. Metal or metal-polymer composites containing one or more of these materials may also be used in forming the support members 20, if desired. In certain embodiments, the support members 20 can be formed from a superelastic material such as a nickel-titanium alloy (Nitinol). Such materials are capable of enduring significant bending without forming residual stresses within the material, allowing the support members 20 to be collapsed into relatively small delivery devices. The ability of the support members 20 to spring back to their original, unstressed state is significant to permit the blood clot filter device 10 to expand to a desired shape when deployed within a blood vessel.

The anchoring members 26 can be formed integral with or as separate elements from the wire, rod, tubing, etc. forming the support members 20. In the illustrative embodiment of FIG. 1, for example, the anchoring members 26 are formed as extensions of the material forming the support members 20. In an alternative embodiment, the anchoring members 26 may comprise separate members that have been attached to the distal end 24 of the support member 20 by adhesive, laser welding, brazing or other suitable method.

A pointed tip portion 28 of each anchoring member 26 can be configured to pierce the vessel wall. The pointed tip portion 28 may be formed, for example, by grinding down a portion of the wire forming the distal end 24 of each support member 20 to form a point. While a pointed structure is specifically illustrated for anchoring members 26 of FIG. 1, it should be understood that other suitable means for securing the blood clot filter device 10 to the vessel wall could be employed. For example, the anchoring member 26 could include a needle, hook, barb prong, wedge, or other suitable attachment member known in the art.

As can be further seen in FIG. 1, at least a portion of the support members 20 can be slidably received within a number of filter tubes 30. Each filter tube 30 can include a first end 32, a second end 34, and an inner lumen 36 configured to slidably receive a corresponding one of the support members 20 therein. The first end 32 of each filter tube 30 may be attached to or formed integrally with an annular-shaped hub 38 that extends circumferentially about the filter legs 14 adjacent to the apical head 12. The second end 34 of each tubular member 30, in turn, can be configured to lie adjacent to the anchoring member 26 at or near the distal end 24 of the support member 20. The filter tubes 30 can have a substantially straight shape along their length, as shown in FIG. 1, or can assume some other desired shape. In the illustrative embodiment of FIG. 1, a small bend or kink 40 located at or near the free end section 18 of the filter legs 14 can be provided to orient a portion of the filter legs 14 in a direction substantially parallel to the inner wall of the blood vessel.

The filter tubes 30 can be formed of one or more segments of sheathing or tubing having a metal, metal alloy, or metal-polymer composition. Examples of suitable materials include stainless steel, platinum, tungsten, nickel-titanium alloy, polyethylene terapthalate (PET), polytetraflouroethylene (PTFE), polyurethane (nylon) fluorinated ethylene propylene (FEP), polyurethane, polypropylene (PP), polyvinylchloride (PVC), polyether-ester, polyester, polyamide, elastomeric polyamides, block polyamide/ethers, polyether block amide (PEBA), silicones, polyethylene, polyether-ether ketone (PEEK), polyimide (PI), and polyetherimide (PEI). The inner lumen 36 of each filter tube 30 may also include a lubricious coating such as a layer of polytetraflouroethylene (PTFE) to reduce friction between the contact surfaces of the filter tube 30 and support member 20.

During implantation within a blood vessel, the filter tubes 30 provide a surface upon which blood clots (emboli) can be collected. To facilitate lysing of the collected blood clots, all or a portion of the filter tubes 30 may include an anti-thrombogenic coating such as herapin (or its derivatives), urokinase, or PPack (dextrophenylalanine proline arginine chloromethylketone). An anti-inflammatory agent such as dexamethasone, prednisolone, corticosterone, budesonide, estrogen, sulfasalazine, mesalamine, or any suitable combination or mixture thereof may also be applied to the filter tubes 30 as well as other locations of the blood clot filter device 10 to prevent inflammation caused by the engagement of the device 10 along the vessel wall.

Figure 2:
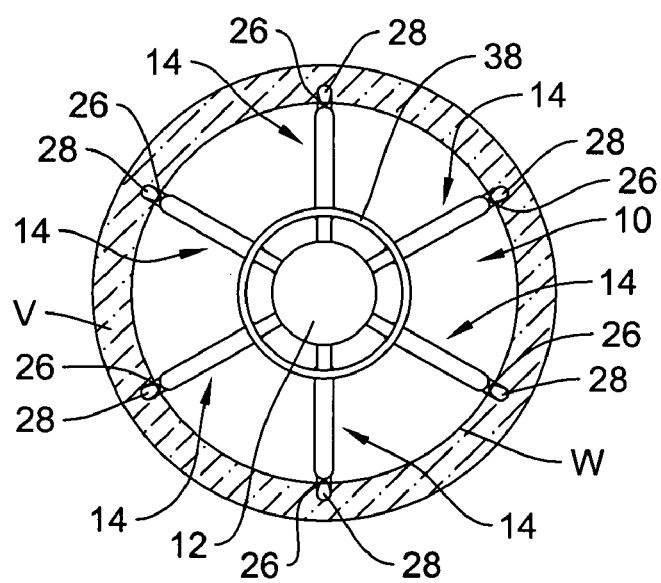
FIG. 2 is a top perspective view showing the illustrative blood clot filter device of FIG. 1 implanted within a blood vessel.

FIG. 2 is a top perspective view showing the blood clot filter device 10 of FIG. 1 implanted within a blood vessel V. As shown in FIG. 2, the filter legs 14 are configured to extend outwardly from the apical head 12 during deployment to anchor the blood clot filter device 10 along the inner wall W of the blood vessel V. The filter legs 14 can be arranged at equidistant intervals such that the filter legs 14 are symmetrically spaced about the longitudinal axis formed by the apical head 12. In the illustrative embodiment of FIGS. 1-2, the blood clot filter device 10 is shown having six filter legs 14 arranged at 60° intervals. It is to be understood, however, that any number or arrangement of filter legs can be employed in accordance with the present invention.

When expanded within the blood vessel V, the pointed tip portion 28 of each anchoring member 26 can be configured to pierce the inner wall of the vessel V. In use, each anchoring member 26 compresses against the inner wall W of the vessel V as a result of the outwardly directed force exerted by the filter legs 14. The amount of force exerted against the inner wall W can be sufficient to prevent migration of the blood clot filter device 10 within the vessel V. By changing design factors such as the dimensions and material composition of the various filter components, the blood clot filter device 10 can be placed in a wide range of vessels within the body.

Figure 3:
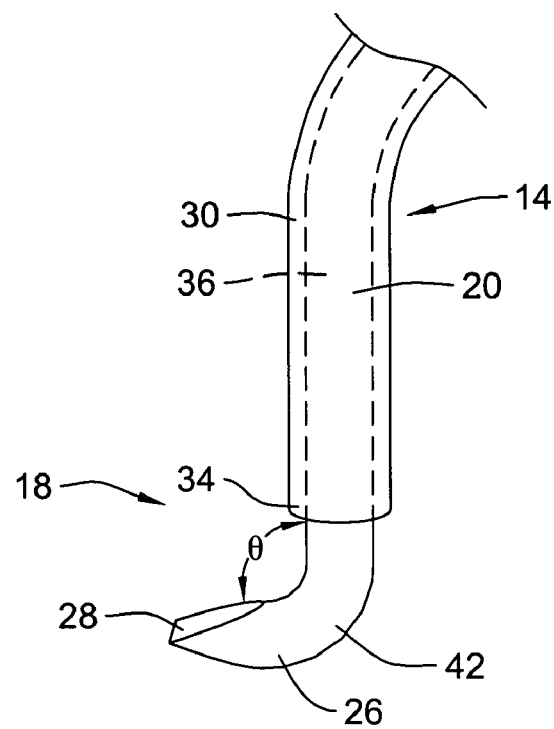
FIG. 3 is an enlarged view showing one of the anchoring members of FIG. 1 in a deployed position.

FIG. 3 is an enlarged view of the free end section 18 of one of the filter legs 14, showing the anchoring member 26 in a deployed position. As shown in FIG. 3, a bending region 42 of the support member 20 orients the anchoring member 26 at an angle θ relative to the support member 20, directing the pointed tip portion 28 towards the inner wall of the blood vessel. The anchoring member 26 can be oriented at any angle θ relative to the support member 20 by applying a bending force thereto. In certain embodiments, for example, the anchoring members 26 can be pre-set to an initial straight position (θ=180°) to facilitate loading of the filter tubes 30 over the support members 20. Once the filter tubes 30 are loaded onto the support members 20, the anchoring members 26 can then be bent to a desired angle θ to orient the pointed tip portions 28 in a direction towards the inner wall of the blood vessel. In some embodiments, the anchoring members 26 can be bent at the bend region 42 to orient the pointed tip portions 28 at an angle substantially perpendicular to the vessel wall W. In other embodiments, the bending region 42 can be configured to orient the pointed tip portions 28 at an acute or obtuse angle relative to the vessel wall W.

Figure 4:
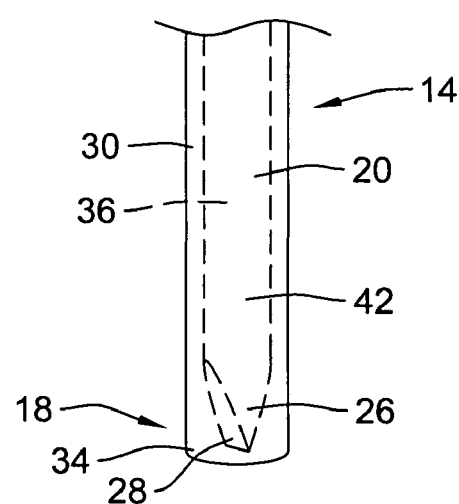
FIG. 4 is an enlarged view showing the anchoring member of FIG. 3 in a retracted position.

FIG. 4 is an enlarged view showing the anchoring member 26 of FIG. 3 in a retracted position. As can be seen in FIG. 4, the anchoring member 26 can be configured to retract into the inner lumen 36 of the filter tube 30. Retraction of the anchoring member 26 into the inner lumen 36 can be accomplished by either advancing the filter tube 30 over the anchoring member 26 while holding the anchoring member 26 stationary, or by advancing of the support member 20 towards the apex of the blood clot filter device 10 while holding the filter tube 30 stationary.

As the anchoring member 26 is being retracted into the inner lumen 36 of the filter tube 30, the force of the filter tube 30 exerted on the anchoring member 26 forces the bending region 42 to bend, causing the anchoring member 26 to align with the support member 20. The amount of force required to bend the anchoring member 26 will typically be greater than the force exerted on the blood clot filter device 10 by the flow of blood within the blood vessel. This prevents the anchoring members 26 from prematurely bending within the blood vessel as a result of spikes in blood pressure, or as a result of incidental shifts or movement of the blood clot filter device 10 within the blood vessel.

The amount of force required to bend the anchoring members 26 can be varied based on a number of factors including, for example, the type of material(s) used to construct the blood clot filter device 10, and the dimensions of the various components employed. In certain embodiments, for example, the bending region 42 can be reduced in profile or include a notch that reduces the stiffness at this region. In other embodiments, the anchoring member 26 may be formed from a flexible material such as Beta III Titanium or a nickel-titanium alloy that can be easily bent without permanently deforming the material.

Figure 5:
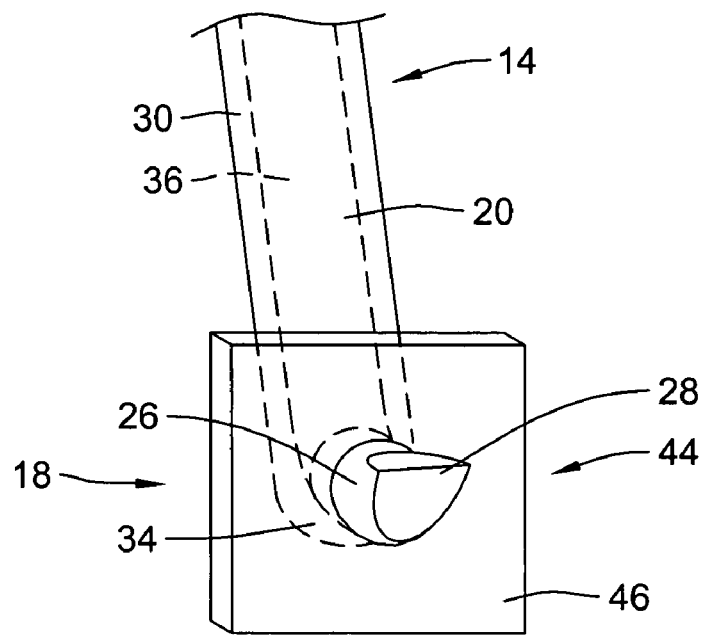
FIG. 5 is an enlarged view showing an alternative anchoring arrangement using a landing pad.

FIG. 5 is an enlarged view showing an alternative anchoring arrangement using a landing pad 44. As shown in FIG. 5, the landing pad 44 can be attached to the distal end 34 of the filter tube 30. The landing pad 44 may be attached to the filter tube 30 at an angle to permit a flat face 46 of the landing pad 44 to lie parallel to and flush with the inner wall of the blood vessel. While a rectangular shaped landing pad 44 is depicted in the illustrative embodiment of FIG. 5, it should be understood that the landing pad 44 could assume any number of desirable shaped. In certain embodiments, for example, the landing pad may have a oval or circular shape with a convex face that approximates the curve of the vessel wall. In use, the landing pad 44 reduces trauma to the body by distributing the force exerted on the wall of the blood vessel by the filter tube 30 over a greater area.

Figure 6:
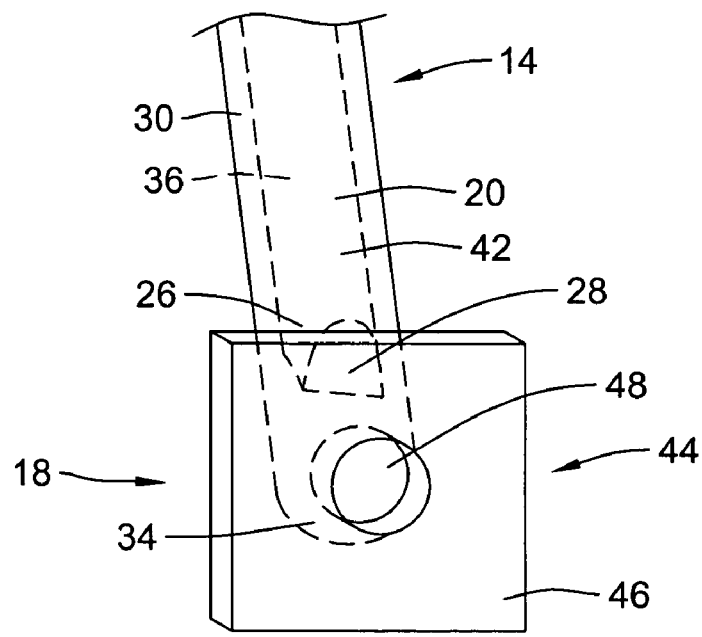
FIG. 6 is an enlarged view showing the anchoring member of FIG. 5 in a retracted position.

FIG. 6 is an enlarged view showing the anchoring member 26 of FIG. 5 in a retracted position. As shown in FIG. 6, an opening 48 originating on the flat face 46 and extending through the thickness of the landing pad 44 can be configured to receive the anchoring member 26 therethrough, allowing the anchoring member 26 to be retracted into the inner lumen 36 of the filter tube 30. Retraction of the anchoring member 26 into the inner lumen 36 of the filter tube 30 can be accomplished by advancing of the support member 20 in a direction towards the apex of the blood clot filter device 10 while holding the filter tube 30 and attached landing pad 44 stationary.

Figure 7:
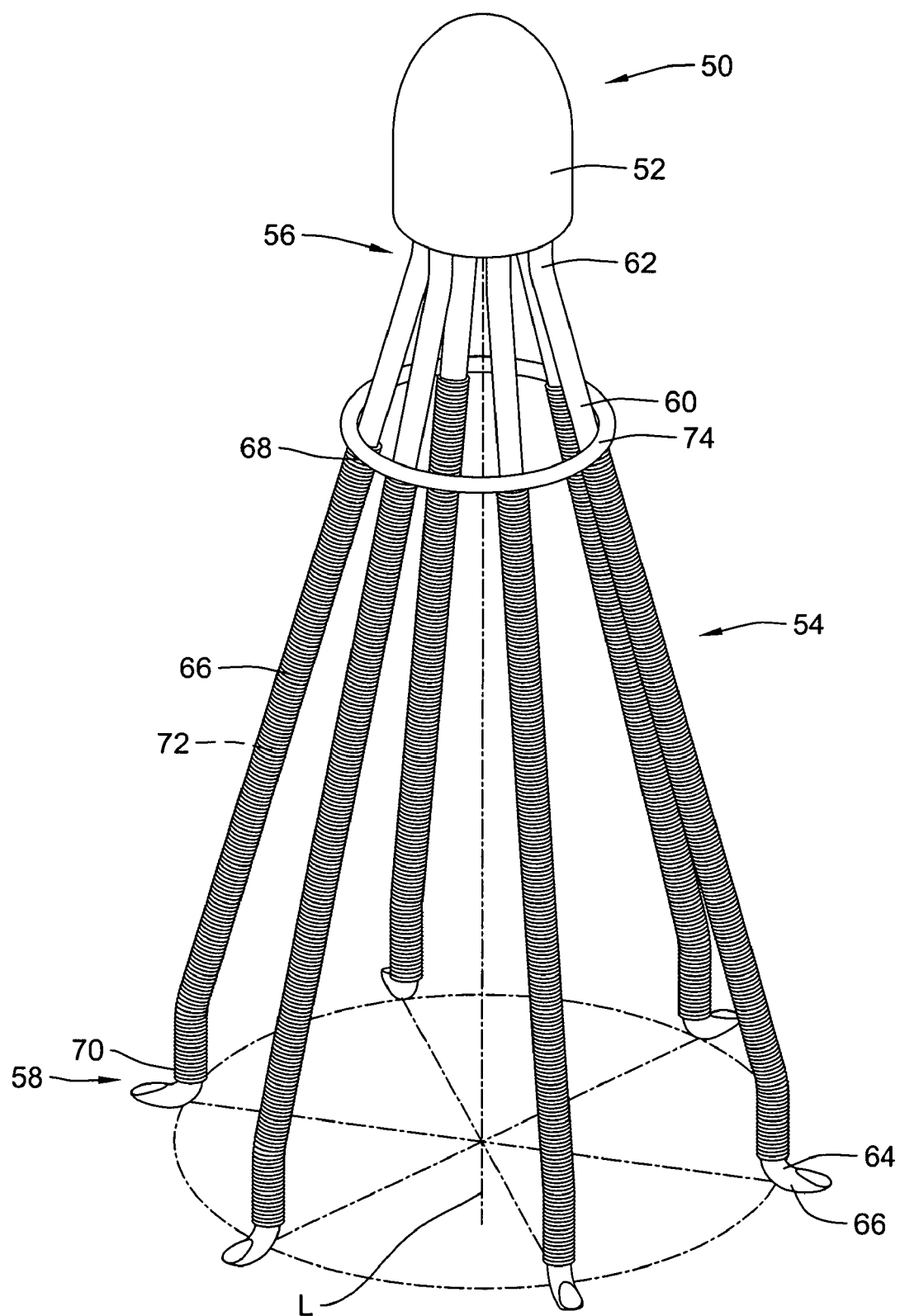
FIG. 7 is a perspective view showing a retrievable blood clot filter device in accordance with another illustrative embodiment of the present invention.

FIG. 7 is a perspective view showing a retrievable blood clot filter device 50 in accordance another illustrative embodiment of the present invention. Similar to blood clot filter device 10 described above, blood clot filter device 50 includes an apical head 52, and a plurality of elongated filter legs 54 each having a joined end section 56 and a free end section 58. Each of the filter legs 54 may include a support member 60 having a first end 62 coupled to the apical head 52, and a second end 64 that extends in an outswept manner to a retractable anchoring member 66 disposed on the free end section 58 of the filter leg 54.

The support members 60 can be slidably received within several coiled filter tubes 66. As shown in FIG. 7, for example, the filter tubes 66 may each comprise a length or segment of coil tubing having a first end 68, a second end 70, and an inner lumen 72 configured to slidably receive a corresponding one of the support members 60 therein. The first end 68 of each coiled filter tube 66 can be attached to or formed integrally with an annular-shaped hub 74 that extends circumferentially about the coiled filter legs 54 adjacent to the apical head 52. The second end 70 of each coiled filter tube 66, in turn, can be configured to lie adjacent to the anchoring member 60.

The coils forming the coiled filter tubes 66 can be tightly spaced together to eliminate any spacing between adjacent coil turns. Alternatively, the coils forming the coiled filter tubes 66 can be loosely spaced, forming several gaps between adjacent coil turns. Each of the coiled filter tubes 66 can be formed by wrapping a wire about a mandrel having an outer diameter slightly larger than the outer diameter of the support members 60 to permit the support members 60 to slide therein. In certain embodiments, the inner lumen 72 of each filter tube 66 may also include a lubricious coating such as a layer of polytetraflouroethylene (PTFE) to reduce friction between the contacts surfaces of the filter tube 66 and support member 60.

Figure 8:
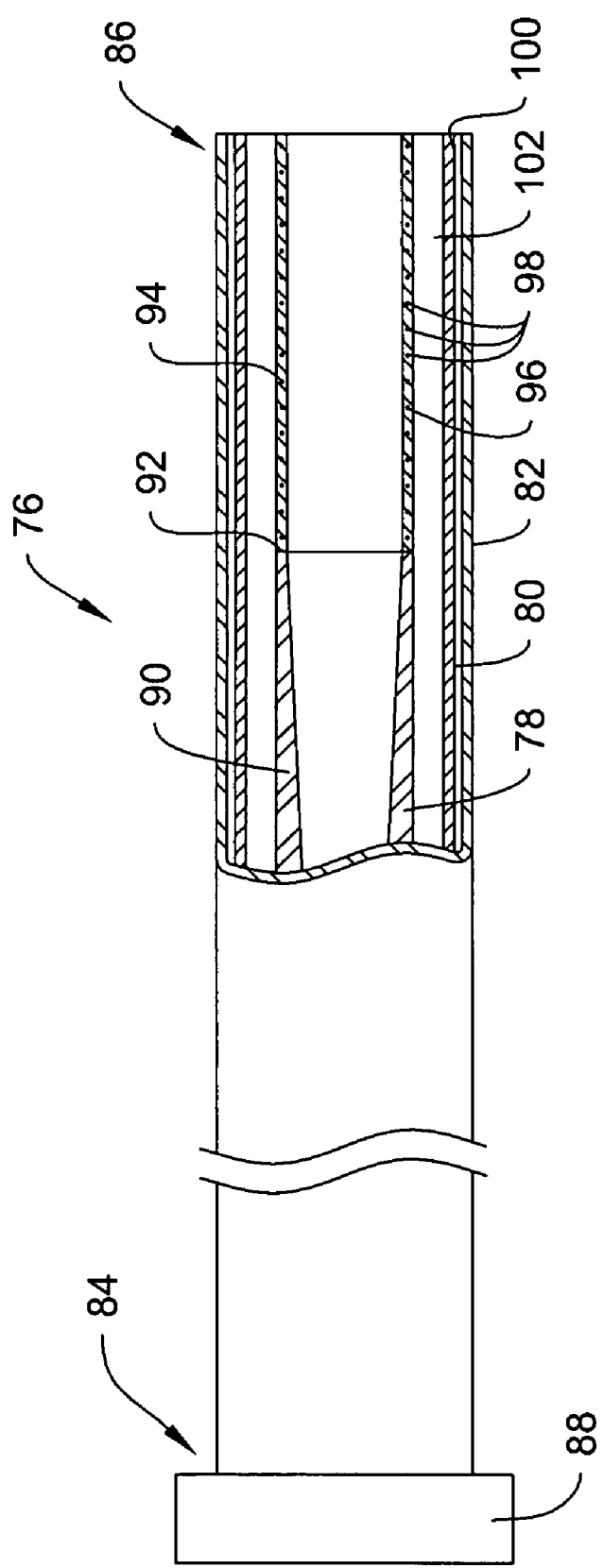
FIG. 8 is a partially broken, longitudinal cross-sectional view showing a retrieval apparatus in accordance with an illustrative embodiment of the present invention.
Figure 9:
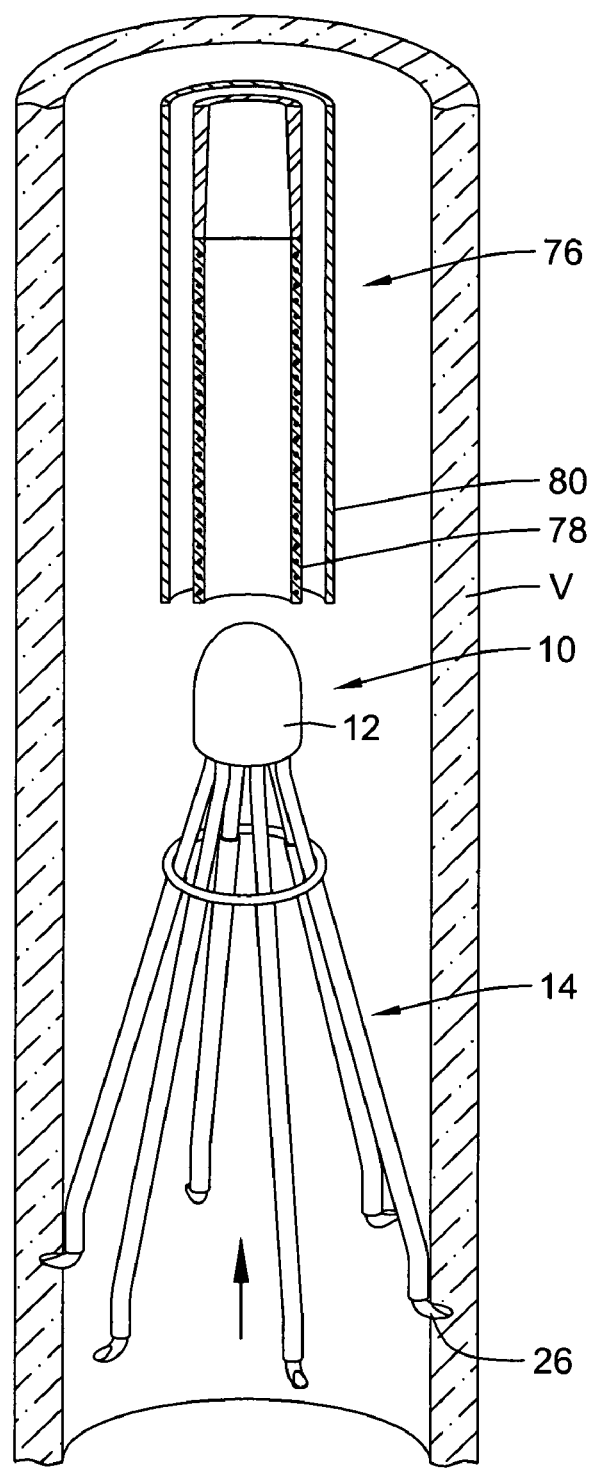
FIG. 9 is a partial cross-sectional view showing the blood clot filter device of FIG. 1 and the retrieval apparatus of FIG. 8 in a first position within a blood vessel.
Figure 10:
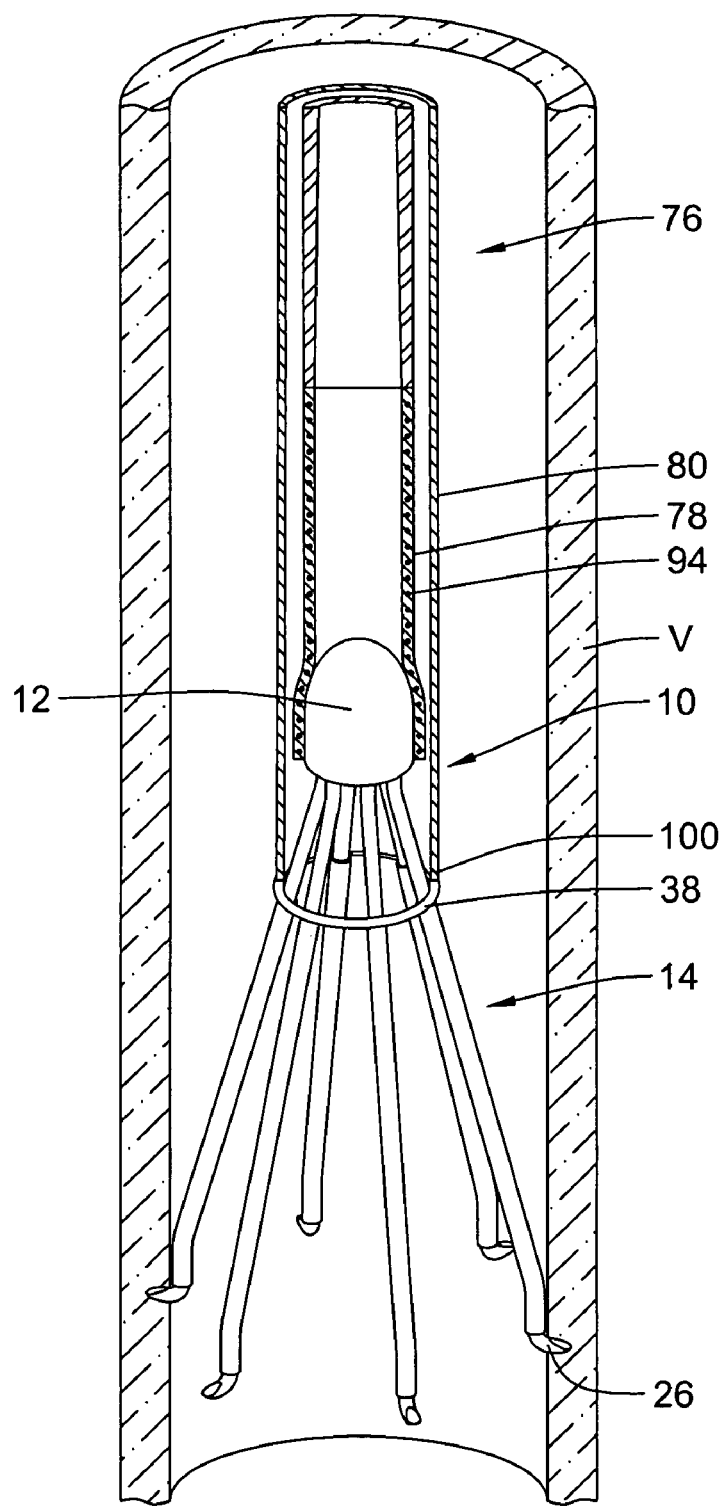
FIG. 10 is a partial cross-sectional view showing the retrieval apparatus in a second position within the blood vessel, wherein the inner member and middle tubular member are shown, respectively, engaging the apical head and hub of the blood clot filter device.
Figure 11:
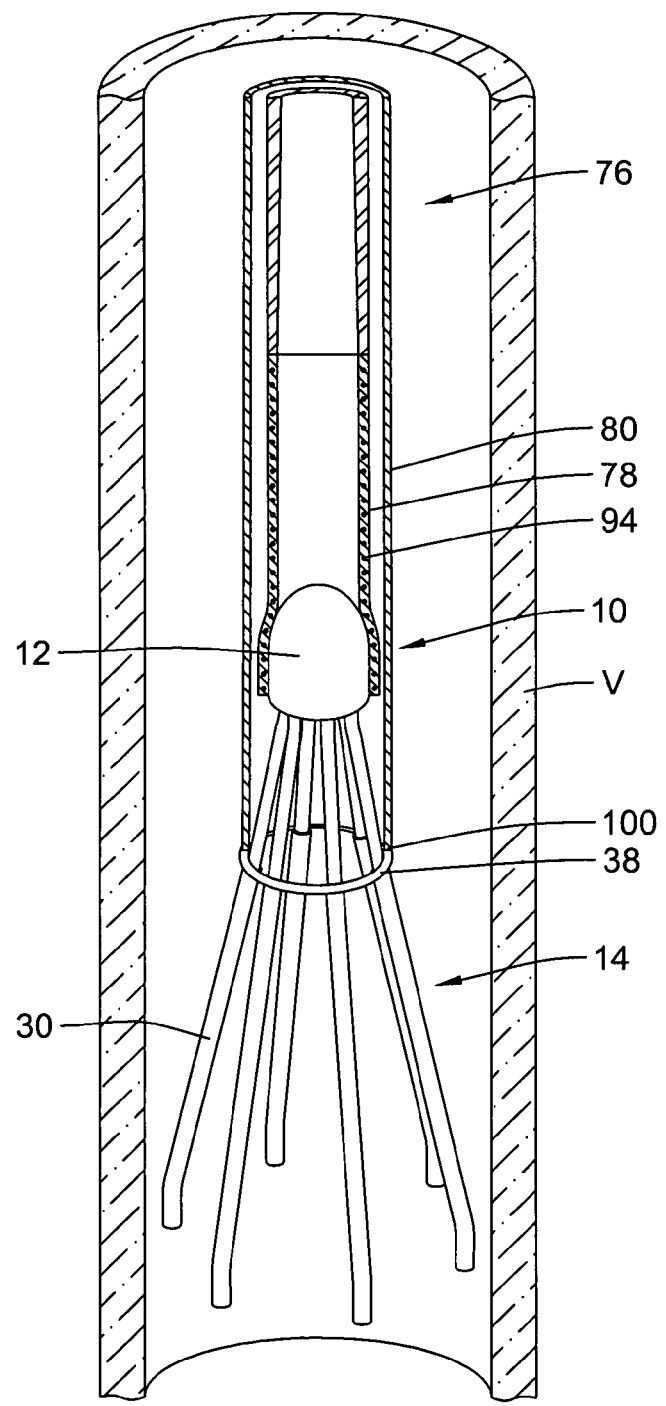
FIG. 11 is a partial cross-sectional view showing the retrieval apparatus in a third position within the blood vessel, wherein the inner member is shown withdrawn proximally to retract the anchoring members within the filter tubes.

FIG. 8 is a partially broken, longitudinal cross-sectional view showing a suitable retrieval apparatus 76 for use in retrieving a medical device such as the blood clot filter device 10 described herein. The retrieval apparatus 76 may comprise a plurality of separate tubular members that can be inserted percutaneously into the body and advanced through the vasculature to the site of the implanted blood clot filter. In the illustrative embodiment of FIG. 8, for example, the retrieval apparatus 76 can include an inner tubular member 78, a middle tubular member 80 slidably disposed about the inner tubular member 78, and an outer sheath 82 slidably disposed about the middle tubular member 78. The arrangement of the various members 78,80,82 can differ, however, depending on the particular filter device being retrieved.

Each of the tubular members 78,80,82 may extend from a proximal end 84 of the retrieval apparatus 76 that can be manipulated from a position outside of the patient's body, to a distal end 86 thereof that can be inserted into the body and advanced to the implantation site to retrieve the blood clot filter from within the blood vessel. A hub 88 disposed at or near the proximal end 84 of the retrieval apparatus 76 can be employed to fix the relative positioning of the tubular members 78,80,82 during the retrieval process.

The inner tubular member 78 can be configured to grasp the apical head 12 of the blood clot filter device 10, allowing the clinician to retract the anchoring members 26 and collapse the filter legs 14 using, respectively, the middle tubular member 80 and outer sheath 82. A proximal segment 90 of the inner tubular member 78 may be formed from a suitable stiff material having sufficient column strength and rigidity to withstand buckling or bulging as the inner tubular member 78 is engaged against the apical head 12. The wall thickness of the proximal segment 90 may be generally uniform along the length of the inner tubular member 78, or may vary to alter the stiffness or torqueability characteristics of the inner tubular member 78, as desired. In the illustrative embodiment of FIG. 8, for example, the proximal segment 90 may decrease in thickness from the proximal end of the inner tubular member (not shown) towards the distal end 92 of the proximal segment 90, wherein the proximal segment 90 transitions into a flexible distal segment 94. It should be understood, however, that the proximal segment 90 may have a constant thickness along its length, or may assume some other desired configuration.

The proximal segment 90 may be formed at least in part from a polymeric material such as polyether block amide (PEBA), which is commercially available from Atochem Polymers of Birdsboro, Pa. under the trade name PEBAX. Other suitable polymeric materials frequently used in the construction of catheters shafts and/or retrieval sheaths may also be employed. The proximal segment 90 may comprise one or more segments having differing material characteristics such as stiffness, torsional rigidity, tensile strength, and/or hardness, if desired.

The distal segment 94 of the inner tubular member 78 can be configured to radially expand when compressed in a direction along its length, allowing the inner tubular member 78 to grasp the apical head 12. The expandability of the distal segment 94 may be due at least in part to the selection of materials used to form the segment 94. Examples of materials that can be used in the construction of the distal segment 94 may include, but are not limited to, polyethylene terapthalate (PET), polytetrafluoroethylene (PTFE), polyurethane (Nylon) fluorinated ethylene propylene (FEP), ethylene tetrafluoroethylene (ETFE), polyurethane, polypropylene (PP), polyvinylchloride (PVC), polyether-ester, polyester, polyamide, elastomeric polyamides, block polyamide/ethers, polyether block amide (PEBA), silicones, polyethylene (PE), polyether-ether ketone (PEEK), polyimide (PI), polyetherimide (PEI), polyphenylene sulfide (PPS), polyphenylene oxide (PPO), polysulfone, perfluoro(propyl vinyl ether) (PFA), or other suitable materials, mixtures, combinations or copolymers thereof. In certain embodiments, the polymeric material may be blended with or otherwise include a liquid crystal polymer (LCP) to enhance torqueability.

The material forming the proximal segment 90 and/or distal segment 94 may include a radiopaque filler such as barium sulfate ($BaSO_4$) or bismuth subcarbonate (($BiO)_2CO_3$) to permit visualization of the retrieval apparatus 76 within the body. Radiopaque materials are understood to be materials capable of producing a relatively bright image on a fluoroscopic monitor or other imaging device. When a radiopaque die is injected into the vessel at issue, the relatively bright image produced on the monitor can be used to determine the location of the inner tubular member 78 within the body.

A braided layer 96 coupled to or formed integrally with the distal segment 94 of the inner tubular member 78 can be utilized to impart expandability to the distal segment 94 while maintaining its desired stiffness and rigidity characteristics. The braided layer 96 may include a number of filaments 98 encased within or disposed adjacent to the distal segment 94. The filaments 98 may be arranged generally in two sets of parallel helices wound in opposite directions about a common longitudinal axis disposed through the center of the inner tubular member 78. The filaments 98 may intersect each other in an overlapping or interwoven fashion to permit the distal segment 94 to radially expand when subjected to a compressive force.

In the exemplary embodiment depicted in FIG. 8, the braided layer 96 extends along the entire length of the distal segment 94, terminating proximally at or near the distal end 92 of the proximal segment 90. In other embodiments, however, the braided layer 96 may extend along only a portion of the distal segment 94, or may extend further into all or a portion of the proximal segment 90.

The filaments 96 can be formed from any number of suitable materials including polymers, metals, metal alloys, metal-polymer composites, or metal-metal composites. Some examples of suitable metals and metal alloys include platinum, stainless steel, Beta III Titanium, nickel-titanium alloy (Nitinol), nickel-chromium alloy, nickel-chromium alloy, cobalt alloy, or the like. Polymers similar to that used in the construction of the proximal and distal segments 90,94 may also be used in forming the filaments 98. The filaments 98, or portions thereof, may also be doped with or otherwise include a radiopaque material to facilitate fluoroscopic visualization within the body. For example, the filaments 98 may be formed at least in part of gold, platinum, palladium, tantalum, tungsten alloy or other suitable radiopaque material capable of producing a relatively bright image on a fluoroscopic screen or other imaging device.

The middle tubular member 80 can be configured to engage the annular-shaped hub 38 and retract the anchoring members 26 into the filter tubes 30. The middle tubular member 80 may comprise a rigid sheath or tube that extends from a proximal end (not shown) to a distal end 100 thereof. An annular spaced gap 102 disposed between the inner tubular member 78 and middle tubular member 80 provides a sufficient amount of clearance to permit the middle tubular member 80 to be advanced beyond the apical head 12 and against the hub 38 once the distal segment 94 of the inner tubular member 78 has been expanded to grasp the apical head 12.

The retrieval apparatus 76 may further include an outer sheath 82 that can be used in collapsing and retrieving the blood clot filter device 10 within the body. The outer sheath 82 may comprise an elongated segment of sheathing or hypodermic tubing having an internal lumen dimensioned to receive the collapsed blood clot filter device 10 therein. In certain embodiments, the outer sheath 82 may comprise the same or similar sheath used to deliver the blood clot filter device 10 to the target (i.e. implantation) site.

Turning now to FIGS. 9-15, an illustrative method of retrieving a blood clot filter will now be described with respect to blood clot filter device 10 and retrieval apparatus 76 described above. In preparation for implantation, the blood clot filter device 10 can be loaded into an introducer sheath and inserted percutaneously into the body in accordance with standard practice in the art. The blood clot filter device 10 is then advanced to a desired vessel within the body (e.g. the inferior vena cava), and removed from within the introducer sheath, causing the filter legs 14 to deploy and engage the wall of the vessel. As the blood clot filter device 10 is deployed, the pointed tip portion 28 on the anchoring member 26 pierces the cava wall W, temporarily fixing the blood clot filter device within the vessel V, as shown, for example, in FIG. 9. In this position, blood flow within the blood vessel (indicated generally by the upwardly directed arrow) can be collected on the exposed surfaces of the apical head 12 and filter legs 14.

After a certain period of time, it may be desirable to remove the blood clot filter device 10 from within the blood vessel V, or to reposition the device 10 at a new location within the blood vessel V. To remove the blood clot filter device 10 from the blood vessel, for example, the retrieval apparatus 76 can be inserted percutaneously into the vasculature and advanced to a position adjacent to the blood clot filter device 10. In the particular view of FIG. 9, the retrieval apparatus 76 is shown inserted via a jugular approach through the jugular vein of the patient.

With the retrieval apparatus 76 advanced to the site of the blood clot filter device 10, the clinician next releases the hub 88 (not shown) and advances the inner tubular member 78 distally within the blood vessel V toward the apical head 12. In a second position illustrated in FIG. 10, the inner tubular member 78 is shown engaged against the apical head 12, causing the distal segment 94 of the inner tubular member 78 to expand and grasp the apical head 12. The middle tubular member 80 is further shown advanced distally toward the blood clot filter device 10, with the distal end 100 thereof seated against the hub 38.

To retract the anchoring members 26 from the vessel wall, the clinician, while holding the blood clot filter device 10 stationary with the middle tubular member 80, retracts the inner tubular member 78 in a proximal direction. Alternatively, the clinician may hold the inner tubular member 78 stationary while advancing the distal end 100 of the middle tubular member 80 against the hub 38. In either case, the movement of the filter tubes 30 about the support members 20 causes the anchoring members 26 to bend and retract into the filter tubes 30, as shown, for example, in FIG. 11.

Figure 12:
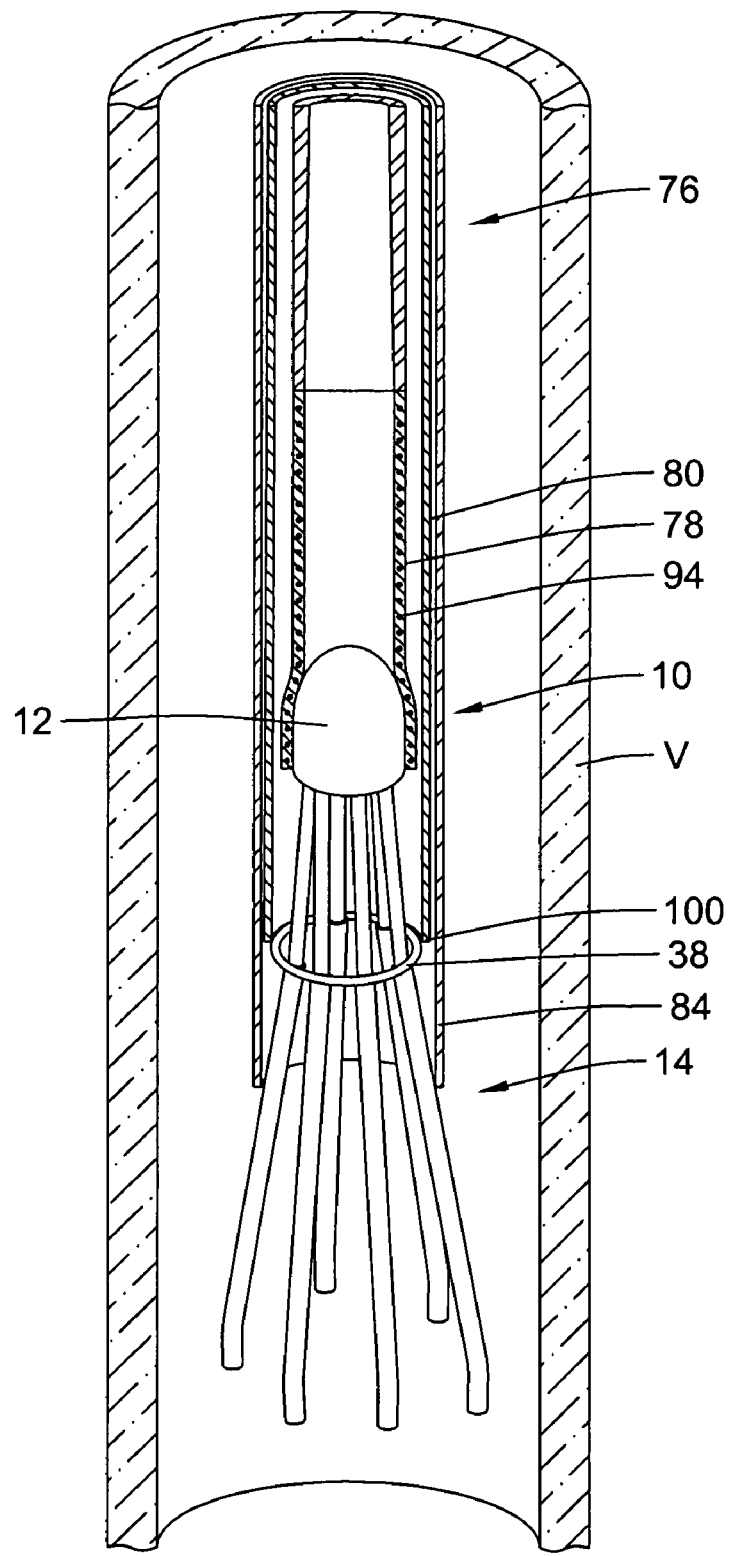
FIG. 12 is a partial cross-sectional view showing the retrieval apparatus in a fourth position within the blood vessel, wherein the filter legs are shown collapsed at least in part within the outer sheath of the retrieval apparatus.
Figure 13:
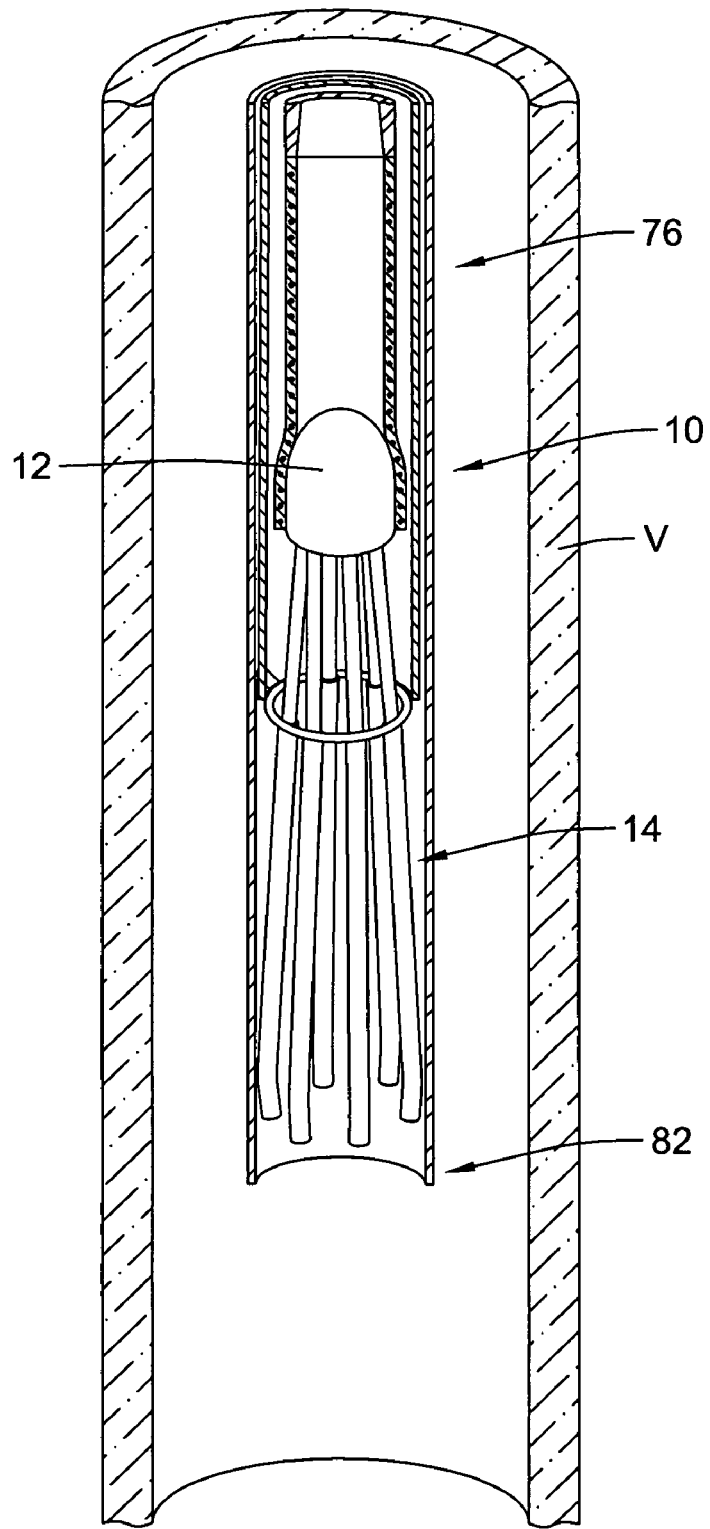
FIG. 13 is a partial cross-sectional view showing the retrieval apparatus in a fifth position within the blood vessel, wherein the blood clot filter device is shown collapsed entirely within the outer sheath of the retrieval apparatus.
Figure 14:
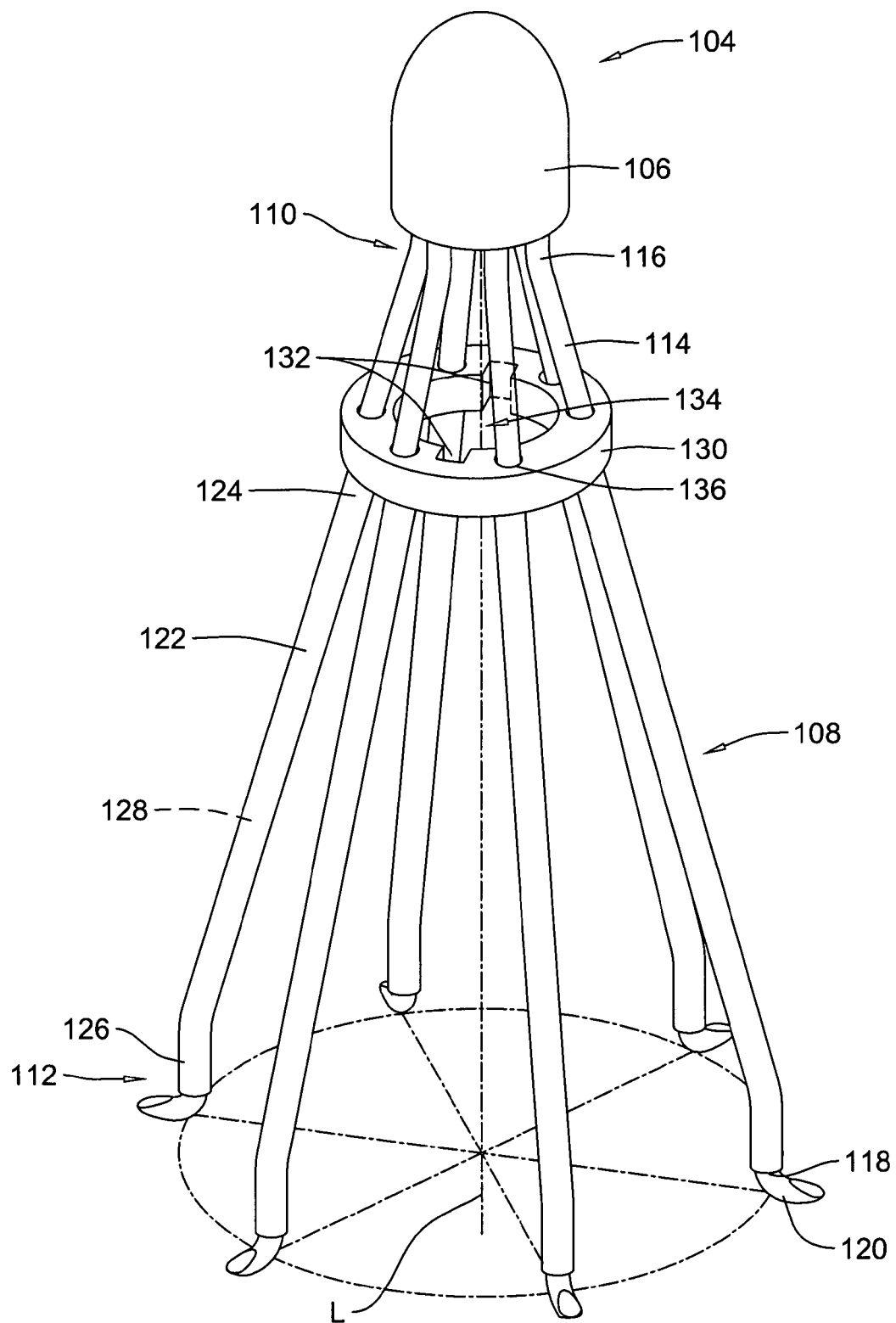
FIG. 14 is a perspective view of a retrievable blood clot filter device in accordance with another illustrative embodiment of the present invention.

With the retractable anchoring members 26 released from the inner wall of the blood vessel V, the clinician can next advance the outer sheath 82 distally about the filter legs 14, causing the filter legs 14 to begin to collapse, as shown, for example, in FIG. 12. Continued advancement of the outer sheath over filter legs 14 causes the blood clot filter device 10 to assume a fully collapsed position, as shown, for example, in FIG. 13, allowing the clinician to either remove the blood clot filter device 10 from the body, or reposition the device 10 at another location within the blood vessel V FIG. 14 is a perspective view of a retrievable blood clot filter device 104 in accordance with another illustrative embodiment of the present invention. Similar to other embodiments discussed herein, the blood clot filter device 104 can include an apical head 106, and a plurality of elongated filter legs 108 each having a joined end section 110 and a free end section 112. Each of the filter legs 108 can include a support member 114 having a first end 116 coupled to the apical head 106, and a second end 118 that extends angularly in an outswept manner to a retractable anchoring member 120 disposed on the free end section 112 of each filter leg 108.

The support members 114 can be slidably received within several filter tubes 122 each having a first end 124, a second end 126, and an inner lumen 128 therein. The first end 124 of each filter tube 122 can be attached to or formed integrally with an annular-shaped hub 130 that extends circumferentially about the filter legs 108 adjacent to the apical head 106. In the illustrative embodiment of FIG. 14, the hub 130 includes a series of notches or slots 132 formed within the interior 134 of the hub 130, which as discussed in greater detail below, can be used in conjunction with a retrieval apparatus to retrieve the blood clot filter device 104 within a Vena Cava via a femoral approach through one of the femoral veins. Several openings 136 (hidden) disposed through the thickness of the hub 130 can be configured to slidably receive the support members 114.

Figure 15:
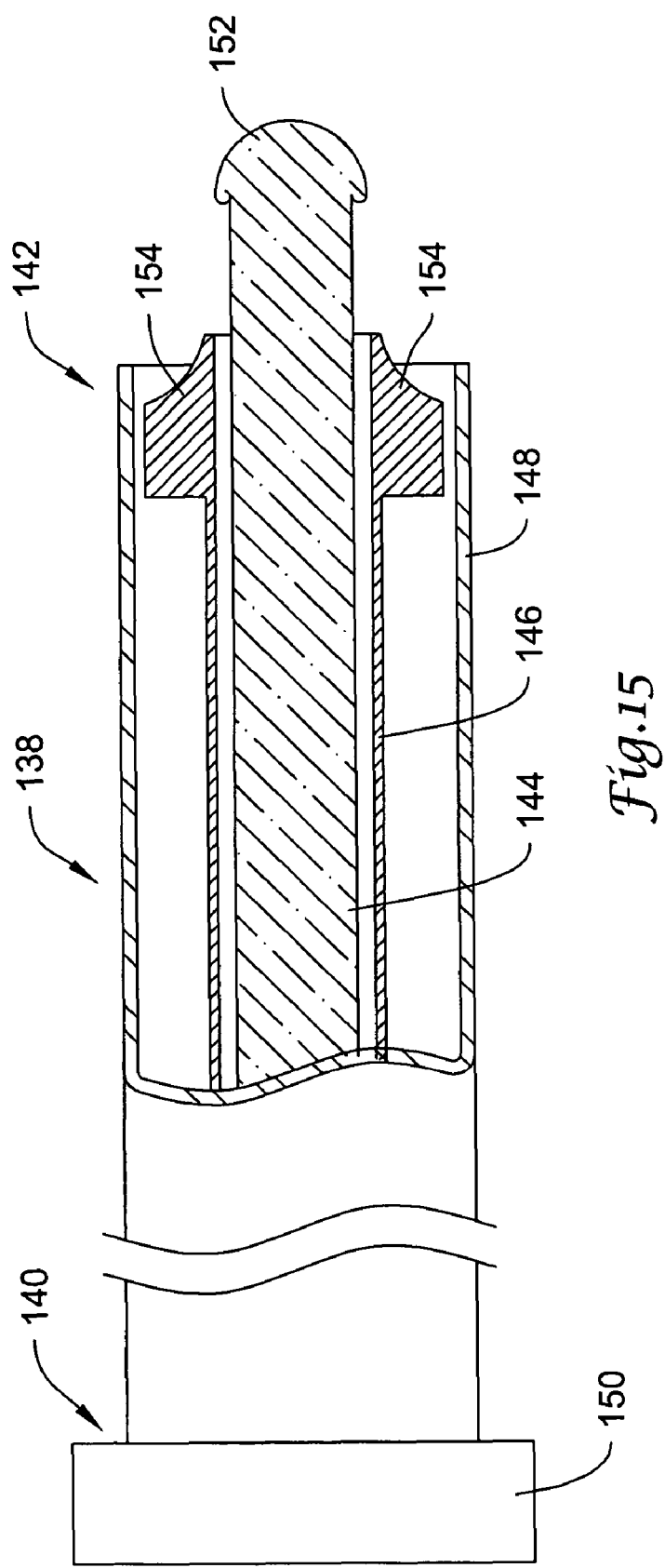
FIG. 15 is a partially broken, longitudinal cross-sectional view showing a retrieval apparatus in accordance with another illustrative embodiment of the present invention.
Figure 16:
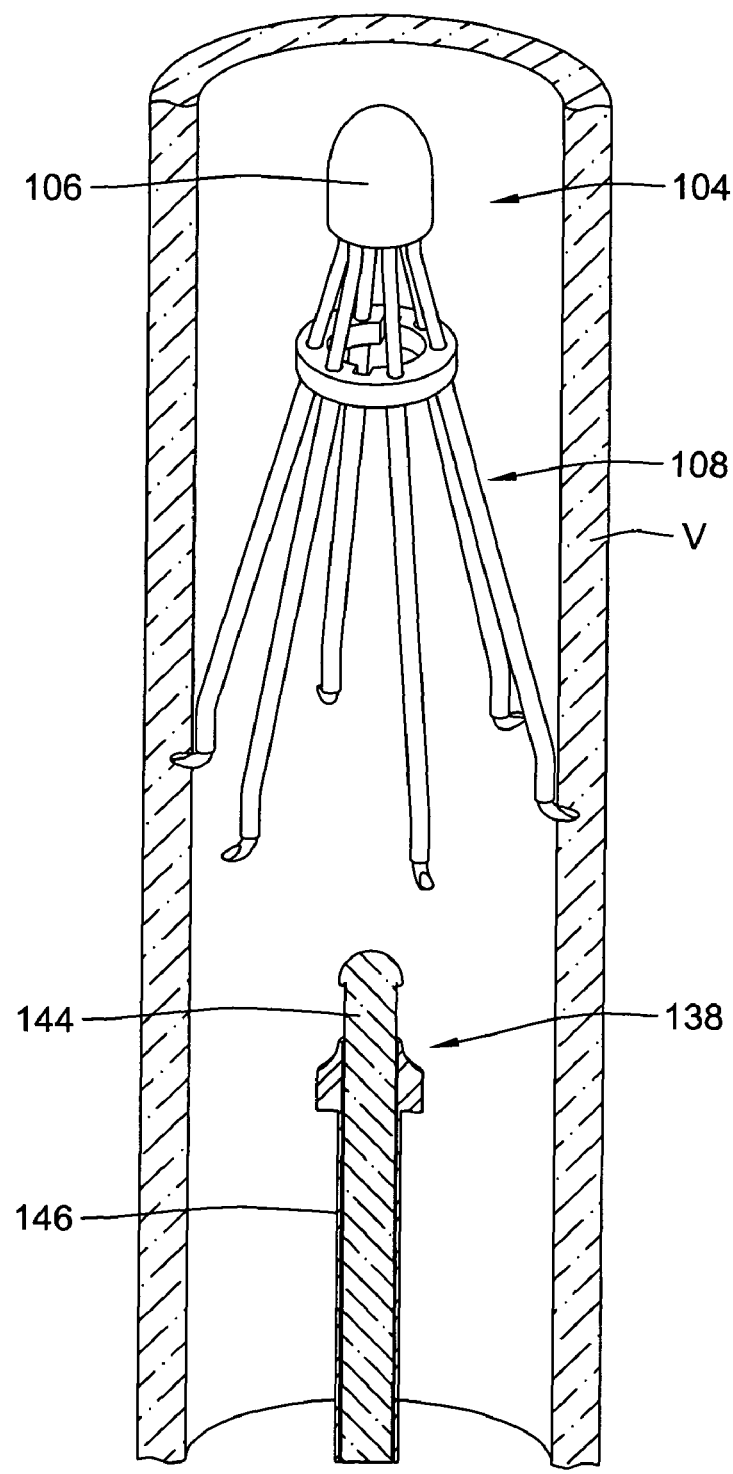
FIG. 16 is a partial cross-sectional view showing the blood clot filter device of FIG. 14 and retrieval apparatus of FIG. 15 in a first position within a blood vessel.
Figure 17:
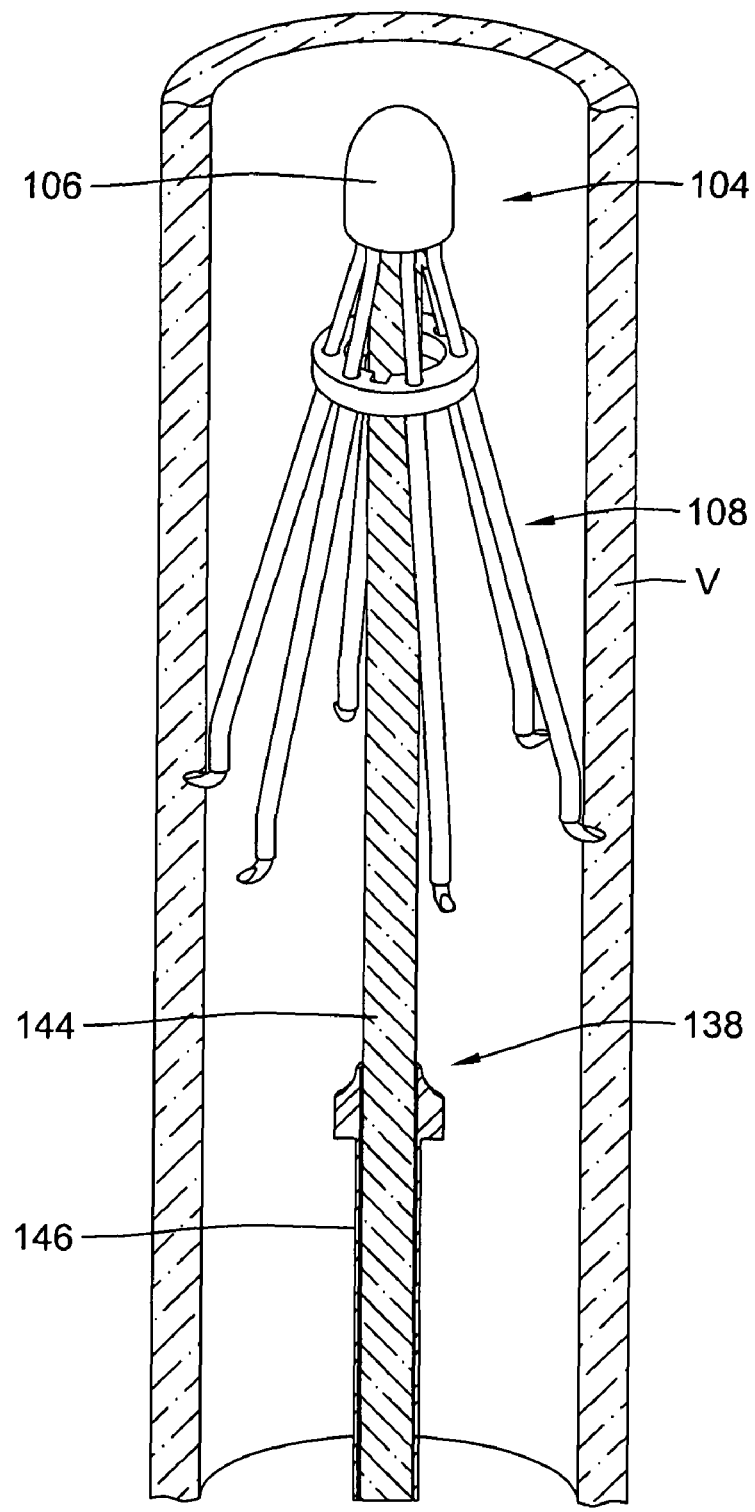
FIG. 17 is a partial cross-sectional view showing the retrieval apparatus in a second position within the blood vessel, wherein the inner member is shown engaging the apical head of the blood clot filter device.
Figure 18:
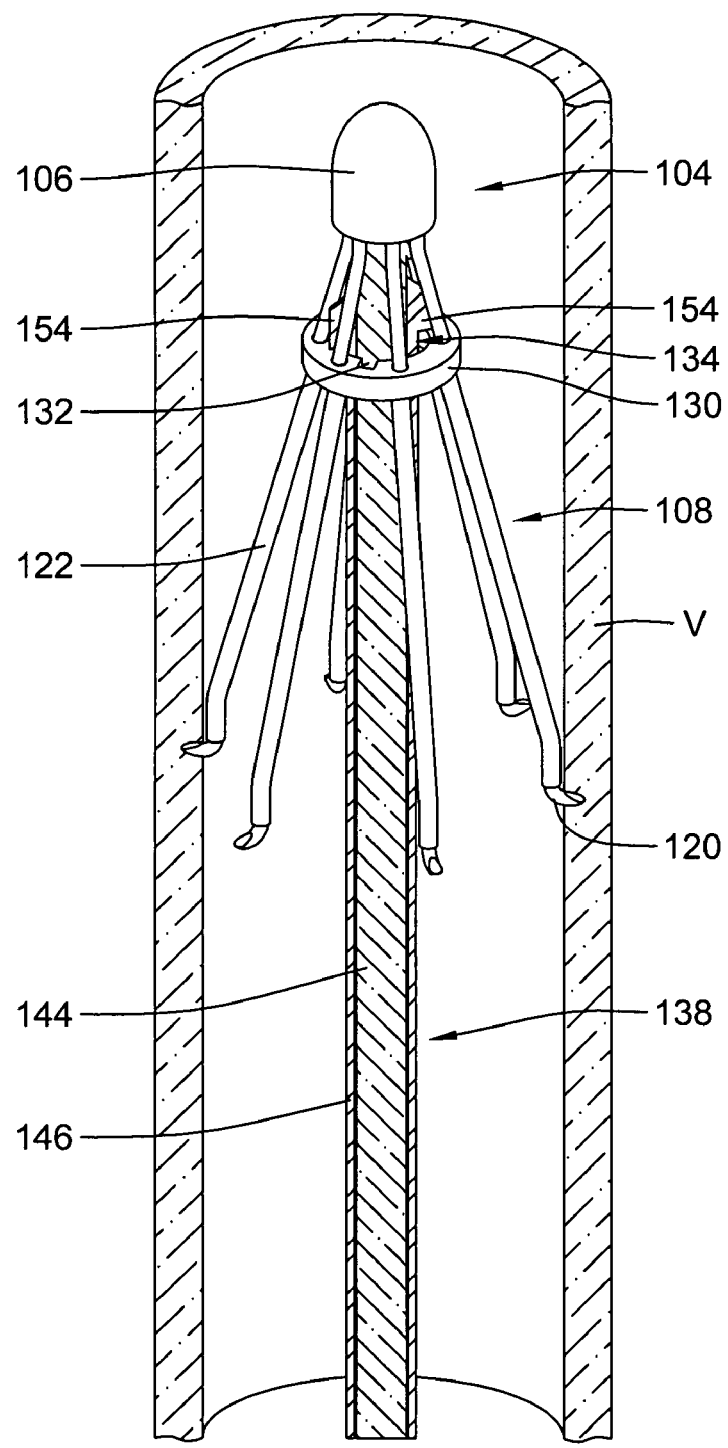
FIG. 18 is a partial cross-sectional view showing the retrieval apparatus in a third position within the blood vessel, wherein the middle tubular member is shown engaging the hub of the blood clot filter device.
Figure 19:
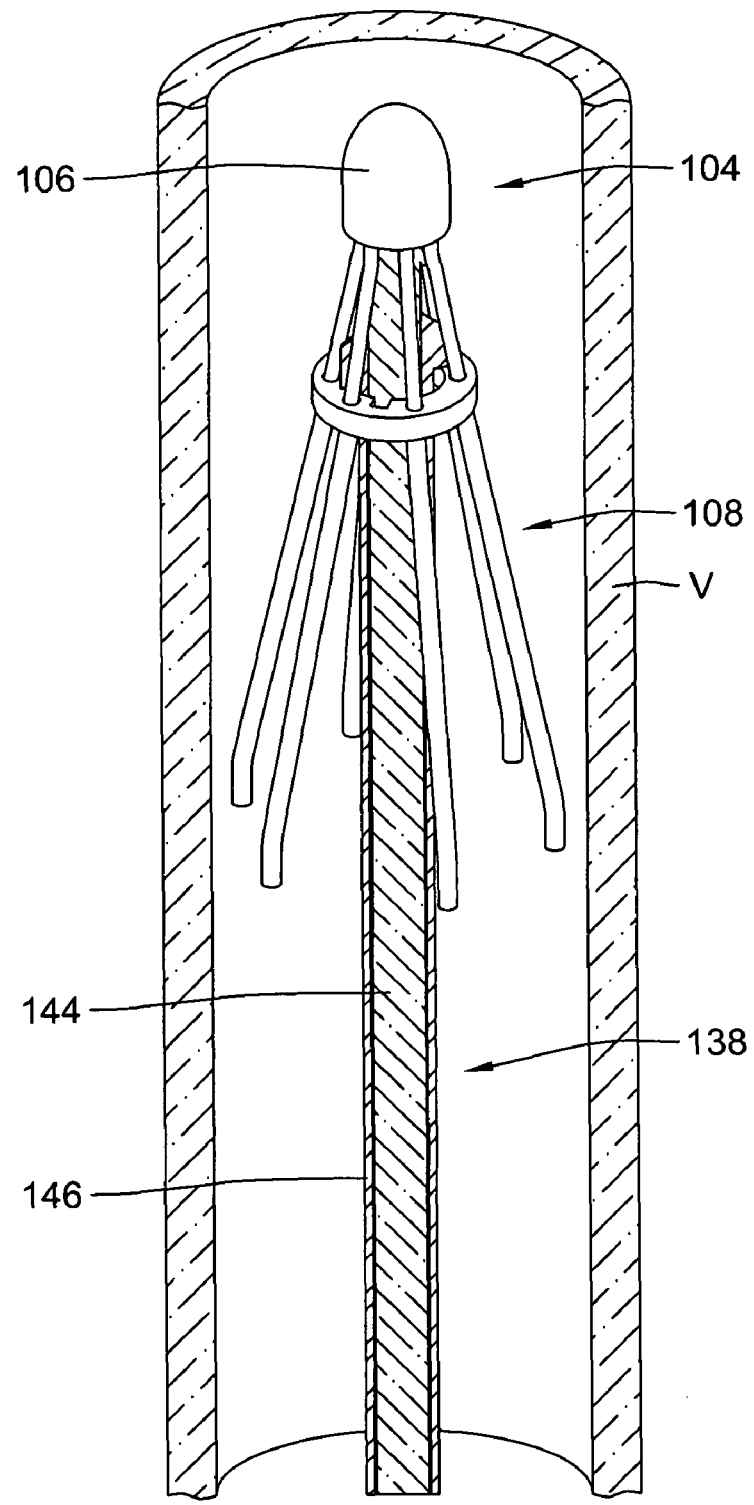
FIG. 19 is a partial cross-sectional view showing the retrieval apparatus in a fourth position within the blood vessel, wherein the inner member is shown advanced distally to retract the anchoring members within the filter tubes.
Figure 20:
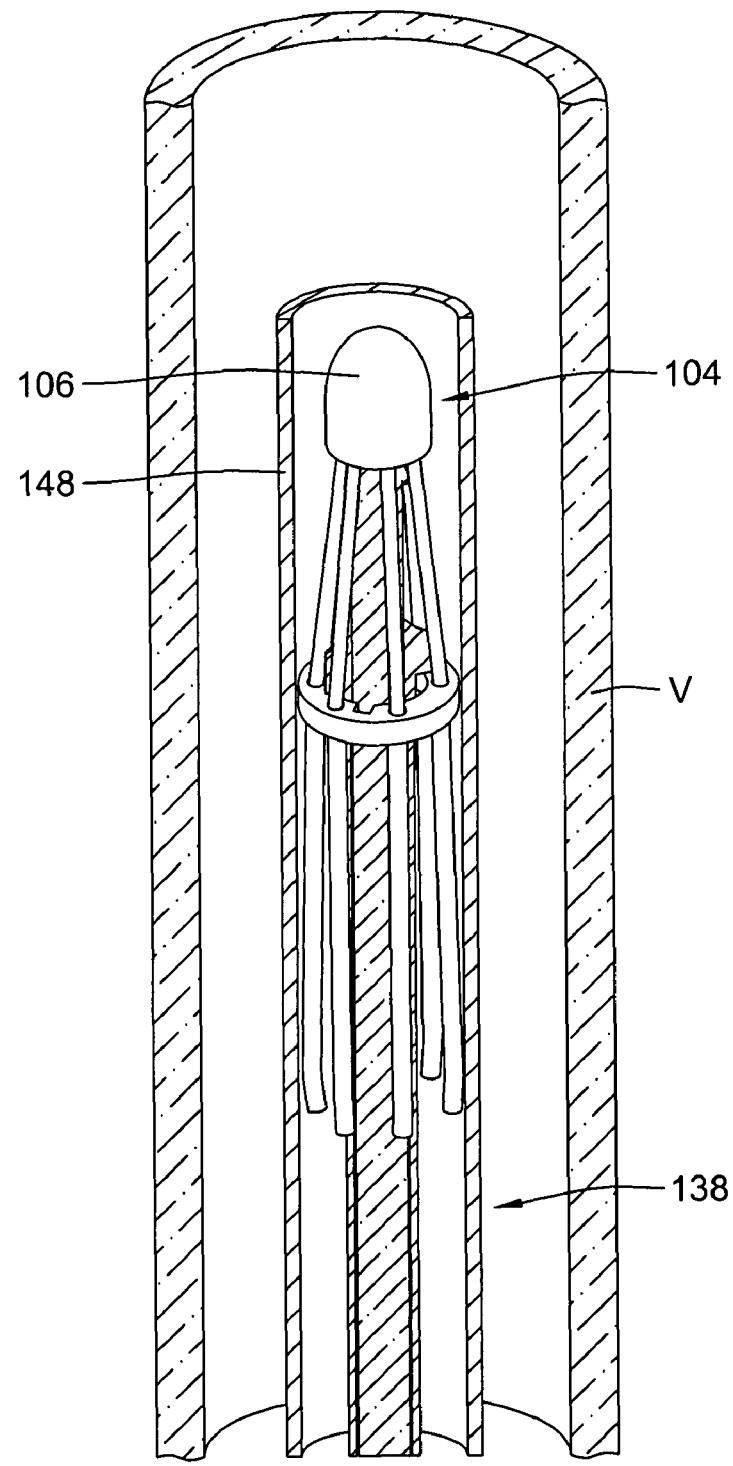
FIG. 20 is a partial cross-sectional view showing the retrieval apparatus in a fifth position within the blood vessel, wherein the blood clot filter device is shown collapsed entirely within the outer sheath of the retrieval apparatus.

FIG. 15 is a partially broken, longitudinal cross-sectional view showing a retrieval apparatus 138 for use in retrieving a medical device such as blood clot filter 104 discussed herein. Similar to the retrieval apparatus 76 discussed above with respect to FIG. 8, retrieval apparatus 138 may include several members that extend from a proximal end 140 of the retrieval apparatus 138 that can be manipulated from a position outside of the patient's body, to a distal end 142 thereof that can be inserted into the body and advanced to the implantation site. In the illustrative embodiment of FIG. 15, for example, the retrieval apparatus 138 may include an inner member 144, a middle tubular member 146 slidably disposed about the inner member 144, and an outer sheath 146 slidably disposed about the middle tubular member 146. A hub 150 disposed at or near the proximal end 104 of the retrieval apparatus 138 can be employed to fix the relative positioning of the members 144, 146,148 during the retrieval process.

The inner member 144 may include a rod or tubing that can be utilized to engage the apical head 106 of the blood clot filter device 104. The inner member 144 can be dimensioned to allow the inner member 144 to be inserted via a femoral approach through the interior 134 of the hub 130 towards the rear of the apical head 106. A bulbous-shaped tip 152 disposed on the distal end of the inner member 144 can be configured to engage the apical head 106.

The middle tubular member 146 may include a suitably rigid tubular member having one or more fins 154 dimensioned to fit within the notches or slots 132 formed within the interior 134 of the hub 130. When properly aligned, the one or more fins 154 on the middle tubular member 146 can be inserted through the interior 134 of the hub 130 in a direction toward the apical head 106. Once inserted through the interior 134 of the hub 130, the middle tubular member 146 can then be rotated slightly (e.g. 90° clockwise or counterclockwise) causing the one or more fins 154 to become misaligned with the notches or slots 130.

The outer sheath 148 can be utilized to collapse and retrieve the blood clot filter device 104, allowing the clinician to either remove or reposition the device 104 within the body. The outer tubular member 148 may comprise a sheath or hypodermic having an internal lumen dimensioned to collapse and receive the blood clot filter device 104 therein. As with other embodiments herein, the outer tubular member 148 may comprise the same or similar sheath used to deliver the blood clot filter device 104 to the target (i.e. implantation) site.

Turning now to FIGS. 16-20, an illustrative method of retrieving the blood clot filter device 104 of FIG. 14 using the retrieval apparatus of FIG. 15 will now be described. In a first position illustrated in FIG. 16, the retrieval apparatus 104 is shown advanced via a femoral approach into a blood vessel V (e.g. the inferior vena cava) adjacent the blood clot filter device 104. With the retrieval apparatus 138 advanced to the site of the blood clot filter device 104, the clinician next advances the inner member 144 distally towards the apical head 106 of the blood clot filter device 104. In a second position illustrated in FIG. 17, the inner member 144 is shown advanced to the apical head 106, causing the bulbous tip 152 to engage the apical head 106.

Once the inner member 144 is engaged against the apical head 106, the clinician may next advance the middle tubular member 146 distally towards the blood clot filter 104 to engage the hub 130. With the one or more fins 154 aligned with the notches or slots 132, the clinician pushes the middle tubular member 146 through the interior 134 of the hub 130 until the one or more fins 154 are disposed beyond the notches or slots 132. The middle tubular member 144 can then be rotated slightly, causing the one or more fins 154 to become misaligned with the notches or slots 132, as shown, for example, in FIG. 18.

To retract the anchoring members 120 within the filter tubes 122, the clinician, while holding the hub 130 stationary with middle tubular member 146, advances the apical head 106 in an upward direction by pushing the inner member 144 distally within the blood vessel V. The advancement of the apical head 106 in this manner causes the anchoring members 120 to bend and retract into the filter tubes 122, as shown, for example, in FIG. 19. Continued advancement of the apical head 104 in this direction causes the filter legs 108 to begin to collapse inwardly, allowing the outer sheath 148 of the retrieval apparatus 138 to be advanced over the filter legs 108 encapsulate the blood clot filter 104 therein, as shown, for example, in FIG. 20. The retrieval apparatus 138 and accompanying blood clot filter device 104 can then be removed from the body, or repositioned at another location within the vessel and redeployed.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. Changes may be made in details, particular in matters of size, shape, and arrangement of parts without exceeding the scope of the invention. It will be understood that this disclosure is, in many respects, only illustrative.

What is claimed is:

1. A retrievable blood clot filter actuatable between a collapsed position and an expanded position within a blood vessel, comprising:

an apical head defining a filter longitudinal axis;

a plurality of elongated filter legs each having a joined end section and a free end section, each filter leg including a support member having a first end coupled to the apical head, and a second end configured to expand outwardly away from the filter longitudinal axis and being coupled to an anchoring member configured to releasably secure the blood clot filter device to the inner wall of the blood vessel;

a plurality of filter tubes each having a first end, a second end, and an inner lumen configured to slidably receive the support members therein, the first end of each filter tube being joined together at a hub, and a landing pad fixedly secured to the second end of each filter tube; and a retrieval apparatus for retrieving or repositioning the blood clot filter device within the blood vessel, the retrieval apparatus including a tubular inner member configured to grasp the apical head, a middle tubular member configured to engage the hub, and an outer sheath for encapsulating the blood clot filter device.

2. The retrievable blood clot filter device of claim 1, wherein said plurality of filter tubes are formed of one or more segments of tubing or sheathing.

3. The retrievable blood clot filter device of claim 1, wherein said plurality of filter tubes are formed of coiled tubing.

4. The retrievable blood clot filter device of claim 1, wherein the anchoring member includes a bending region.

5. The retrievable blood clot filter device of claim 1, wherein the hub is an annular-shaped hub.

6. The retrieval blood clot filter device of claim 5, wherein the annular-shaped hub includes one or more internal notches or slots formed therein.

7. The retrievable blood clot filter device of claim 1, wherein said retrieval means includes a retrieval apparatus configured to retrieve the blood clot filter device using a jugular approach.

8. A filter system, comprising:

a retrievable blood clot filter device including an apical head, and a plurality of elongated filter legs each having a joined end section and a free end section, each filter leg including a support member having a first end coupled to the apical head, and a second end coupled to an anchoring member configured to releasably secure the blood clot filter device to the inner wall of a blood vessel;

a plurality of filter tubes each having a first end, a second end, and an inner lumen configured to slidably receive the support members therein, the first end of each filter tube being coupled to a hub; and a retrieval apparatus for retrieving or repositioning the blood clot filter device within the blood vessel, the retrieval apparatus including an inner member configured to grasp the apical head, a middle tubular member configured to engage the hub, and an outer sheath for encapsulating the blood clot filter device.

9. The filter system of claim 8, wherein said plurality of filter tubes are formed of one or more segments of tubing or sheathing.

10. The filter system of claim 8, wherein said plurality of filter tubes are formed of coiled tubing.

11. The filter system of claim 8, further comprising a landing pad coupled to the second end of each filter tube.

12. The filter system of claim 8, wherein the anchoring member includes a bending region.

13. The filter system of claim 8, wherein the hub is an annular-shaped hub.

14. The filter system of claim 13, wherein the annular-shaped hub includes one or more internal notches or slots formed therein.

15. The filter system of claim 14, wherein said middle tubular member includes one or more fins insertable through said one or more notches or slots.

16. The filter system of claim 8, wherein said inner member comprises a braided tubular member.

17. The retrievable blood clot filter device of claim 8, wherein the retrieval apparatus is configured to retrieve the blood clot filter device using a jugular approach.

18. The retrievable blood clot filter device of claim 8, wherein the retrieval apparatus is configured to retrieve the blood clot filter device using a femoral approach.

19. The filter system of claim 8 wherein the inner member has a cylindrical distal section.

20. The filter system of claim 19 wherein the inner member distal section is configured to radially expand when compressed in a direction along its length.

21. The filter system of claim 20 wherein the distal section comprises a braided layer.

22. The filter system of claim 8 wherein the inner member is tubular.

* * * * *